United States Patent [19]

Vanstraceele et al.

[11] Patent Number: 6,162,451
[45] Date of Patent: *Dec. 19, 2000

[54] CLEANSING OR MAKEUP REMOVING COMPOSITION COMPRISING A POLYHOLOSIDE AND METHODS FOR PREPARING AND USING THIS COMPOSITION

[75] Inventors: Anne Vanstraceele, Paris; Catherine Marion, Sceaux, both of France

[73] Assignee: L'Oreal, Paris, France

[ * ] Notice: This patent is subject to a terminal disclaimer.

[21] Appl. No.: 09/288,964

[22] Filed: Apr. 9, 1999

Related U.S. Application Data

[63] Continuation of application No. 08/781,210, Jan. 10, 1997, Pat. No. 5,928,653.

[30] Foreign Application Priority Data

| Jan. 10, 1996 | [FR] | France | 96 00222 |
| May 21, 1996 | [FR] | France | 96 06287 |
| Jul. 9, 1996 | [FR] | France | 96 08537 |

[51] Int. Cl.$^7$ ..................................................... A61K 7/48
[52] U.S. Cl. .......................... 424/401; 514/844; 514/845; 514/846; 514/944
[58] Field of Search ........................... 424/401; 514/844, 514/845, 846, 944

[56] References Cited

U.S. PATENT DOCUMENTS

| Re. 28,781 | 4/1976 | Konig et al. . | |
| 5,100,879 | 3/1992 | Ueno et al. . | |
| 5,518,733 | 5/1996 | Lamothe et al. . | |
| 5,603,926 | 2/1997 | Matsumoto et al. | 424/70.15 |
| 5,928,753 | 7/1999 | Vanstraceele et al. | 424/401 |

FOREIGN PATENT DOCUMENTS

| 285 829 | 10/1988 | European Pat. Off. . |
| 651 990 | 5/1995 | European Pat. Off. . |
| 2250998 | 6/1992 | United Kingdom . |
| 92/06778 | 4/1992 | WIPO . |
| 93/00067 | 1/1993 | WIPO . |
| 93/07855 | 4/1993 | WIPO . |

*Primary Examiner*—Jyothsan Venkat
*Attorney, Agent, or Firm*—Finnegan, Henderson, Farabow, Garrett & Dunner, L.L.P.

[57] ABSTRACT

The use of at least one homogeneous polyholoside in a cleansing and/or makeup remover composition for the skin and/or mucosae and/or eyes, comprising a cosmetically or dermatologically acceptable vehicle is disclosed, as is a composition for cleansing and/or removing makeup from the skin and/or mucosae and/or eyes, which comprises at least one homogeneous polyholoside.

27 Claims, No Drawings

CLEANSING OR MAKEUP REMOVING COMPOSITION COMPRISING A POLYHOLOSIDE AND METHODS FOR PREPARING AND USING THIS COMPOSITION

This is a continuation of application Ser. No. 08/781,210, filed Jan. 10, 1997 now U.S. Pat. No. 5,928,653, which is incorporated herein by reference.

The present invention relates to the use of a polyholoside in a composition, in particular a cosmetic composition, intended for cleansing and/or for removing makeup from the skin, mucosae, and/or eyes.

It is known to use makeup-removing oils in compositions for removing makeup from the skin and/or eyes. In general, these compositions likewise comprise surfactants, which make it possible to improve the removal of the oil and/or traces of makeup. However, it is known that the use of these compositions may leave an impression of discomfort, especially on the eyelids and/or on the eyes.

Also known are makeup remover compositions based solely on surfactants, making it possible to remove traces of makeup while facilitating the emulsification of the composition by rendering the fatty and aqueous phases of the composition compatible when this composition is in the form of an emulsion. Nevertheless, the surfactants may have the disadvantage of being more or less irritating to the skin.

The object of the present invention is to overcome the disadvantages of the prior art and to provide a composition which permits simple and adequate cleansing and/or makeup removal, which is not irritating to the skin and/or eyes, and which preferably does not contain any surfactant.

One subject of the invention is therefore a composition for cleansing and/or removing makeup from the skin, mucosae and/or eyes, comprising, and preferably consisting essentially of, a homogeneous polyholoside, wherein the homogeneous polyholoside is present in an amount effective to cleanse and/or remove makeup from the skin, mucosae, and/or eyes. It is possible for the at least one homogeneous polyholoside to be contained in a compound, for example a natural product such as honey, which compound is included in the composition of the present invention to provide the at least one homogeneous polyholoside.

Another subject of the invention is the use of a homogeneous polyholoside in a cleansing and/or makeup removing composition for the skin, mucosae, and/or eyes, preferably the composition consists essentially of a homogeneous polyholoside. Preferably the composition further comprises a cosmetically or dermatologically acceptable vehicle, in particular as a cleansing and/or makeup-removing agent, and/or as an agent to obtain a makeup removing composition which causes little or no irritation, and/or to obtain a composition which has a gentle feel, and/or to obtain a gelled composition.

Another subject of the invention is a method for cleansing and/or removing makeup from the skin, mucosae, and/or eyes, which method includes a composition as defined above being applied to the skin, mucosae, and/or eyes.

What has in fact been found by the Inventors is that the use of a polyholoside according to the invention makes it possible to obtain a cleansing and/or makeup removing composition which is effective, non-irritating and low in tackiness and which additionally has a pleasant and gentle feel.

Moreover, the incorporation of a polyholoside into compositions, especially cosmetic compositions, makes it possible to obtain a gelled composition without the further addition of a conventionally employed gelling agent. The gel obtained is smooth and creamy.

The present invention therefore provides for the use of a homogeneous polyholoside as a makeup-removing agent and/or in a makeup removing composition.

The saccharides, of formula $C_n(H_2O)_n$, are generally divided into two categories: the oses, or simple sugars, and the osides, or combinations of several molecules. Among the osides, a distinction may be made between the holosides, which are formed only of sugars, and the heterosides, which contain one or more oses and a non-glucidic part. Among the polyholosides, a further distinction may be made between the homogeneous polyholosides, which result from the combination of a single ose, and the heterogeneous polyholosides, which result either from the combination of different oses or from the combination of oses having the same empirical chemical formula but different geometric configurations (D and L isomers, for example).

Thus the polyholosides according to the invention are homogeneous, and therefore consist solely of sugars and result from the combination of a single ose. However, they may be substituted, especially by fatty chains or amino groups.

The polyholosides according to the invention can preferably comprise chiefly 2 to 10 times the same ose (oligoholosides), or more than 10 times the same ose. The polyholosides according to the invention can also preferably comprise chiefly a single ose unit, selected from all the possible ose units, whether natural or synthetic in origin, and especially:

aldoses, such as pentoses (ribose, arabinose, xylose or apiose, for example) and hexoses (glucose, fucose, mannose or galactose, for example), ketoses, such as fructose, deoxyoses, such as rhamnose, digitoxose, cymarose and oleandrose, and ose derivatives such as the uronic acids, for example, mannuronic, guluronic, galacturonic and glycuronic acid, or else itols, such as mannitol and sorbitol.

Among the polyholosides according to the invention, mention may be made of:

chitin and its derivatives, such as chitosan derivatives, and especially chitosan lactate which is an N-substituted polyholoside;

derivatives of hyaluronic acid, such as the metal salts, and especially sodium hyaluronate which is an N-substituted polyholoside;

dextran and its derivatives, such as dextran sulphate;

cellulose and its derivatives, such as cellulose gum, hydroxyethylcellulose, hydroxypropylcellulose, polyquaternium 10, and polyquaternium 24;

starch, amylose and amylopectin and their derivatives; and chondroprotein and its derivatives, such as chondroitin and chondroitin sulphate.

It is also possible to use compounds that contain polyholosides according to the invention, especially natural products such as honey, which product contains approximately 10% dextrin.

The polyholosides according to the invention may be branched or linear. They can also be substituted, for example by fatty chains, especially those containing from 8 to 30 carbon atoms, and/or by amino groups.

Within the scope of the present invention, it is possible to use a single homogeneous polyholoside or a mixture of homogeneous polyholosides.

The polyholosides according to the invention are preferably introduced into the composition in the form of an aqueous solution which may contain from 0.01 to 5% by weight of polyholoside.

The polyholosides are preferably present in the final composition in a quantity of from 0.01 to 5% by weight, more preferably from 0.02 to 1% by weight, relative to the total weight of the composition.

The polyholosides according to the invention can therefore be used as makeup-removing agents, especially in a composition for cleansing and/or removing makeup from the skin of the body or face, from the mucosae, such as the lips, and/or from the eyes.

They may also replace some or all of the surfactants which are generally present in the prior art cleansing and/or makeup removing compositions.

The composition may be in the form of an emulsion, especially an oil-in-water or water-in-oil emulsion, or even in the form of a multiple emulsion. It may also be present in the form of an aqueous solution, which may be gelled, or in the form of a lotion, for example a biphase lotion, or a cream, milk or mousse.

The compositions according to the invention may comprise an oily phase which is based on animal, vegetable, mineral, silicone, fluorinated and/or synthetic oil. The oily phase may also comprise fatty alcohols or fatty acids, surfactants and emulsifiers. Particular mention may be made of the hydrocarbon oils, such as paraffin oil or vaseline oil; perhydrosqualene; groundnut oil; sweet almond oil; calophyllum oil; palm oil; castor oil; avocado oil; jojoba oil; olive oil; and cereal germ oils; and alcohols such as oleyl alcohol, linoleyl alcohol, linoleneyl alcohol, isostearyl alcohol and octyldodecanol. It is also possible to mention silicone oils such as PDMS, which may be phenylated such as the phenyltrimethicones.

The oily phase may also comprise a makeup-removing oil, such as a fatty acid ester, in particular the esters obtained from an alcohol having a straight or branched chain of from 1 to 17 carbon atoms and from a fatty acid having a straight or branched chain of from 3 to 18 carbon atoms. An ester of this kind may in particular be chosen from the group containing dioctyl adipate, 2-ethylhexyl palmitate, diisopropyl adipate, 2-ethylhexyl hexanoate, ethyl laurate, ethyl myristate, octyldodecyl octanoate, isodecyl neopentanoate, ethyl myristate, myristyl propionate, 2-ethylhexyl 2-ethylhexanoate, 2-ethylhexyl octanoate, 2-ethylhexyl capratelcaprylate, methyl palmitate, butyl myristate, isobutyl myristate, ethyl palmitate, isohexyl laurate, hexyl laurate and isopropyl isostearate.

The oily phase may be present in a proportion ranging from 5 to 95% by weight in the case of an emulsion.

The composition according to the invention may comprise, in addition, an agent which makes it possible to suspend the fatty phase, for example a copolymer of $C_{10}$–$C_{30}$ alkyl acrylates and acrylic or methacrylic acid or an ester thereof (Pemulen TR1, Pemulen TR2, Carbopol 1342 from Goodrich) or an acrylamidemethylpropanesulfonic acid copolymer (Sepigel from SEPPIC), and/or an agent for dispersing the fatty phase, such as an emulsifying or vesicular system based on vesicles, optionally of nanometric size, which are made up of ionic lipids (liposomes) or nonionic lipids, and especially the emulsifying systems which are well known to the skilled worker and contain glyceryl stearate/PEG 100 stearate (CTFA), cetyl alcohol and stearyl alcohol.

The composition of the invention may additionally comprise an agent for modifying its viscosity and may reach textures which are gelled to a greater or lesser extent, such as:

cellulose derivatives (carboxymethylcellulose, hydroxyethylcellulose, hydroxypropylmethylcellulose), natural gums, such as xanthan, guar and carob gums, and scleroglucans, chitin derivatives, chitosan derivatives, and carragheenans, and polycarboxyvinyl derivatives of the Carbomer type (sold by Goodrich under the names Carbopol 940, 951, 980, or by 3V-SIGMA under the name Synthalen K or Synthalen L).

The composition according to the invention may additionally comprise, as is known, adjuvants which are commonly used in the field under consideration, such as preservatives, antioxidants, fragrances, fillers such as kaolin or starch, or even hollow microspheres, pigments, UV filters, sequestrants, essential oils, colorants, hydrophilic or lipiphilic active agents, such as moisturizers, especially glycerol, butylene glycol, anti-inflammatories such as allantoin, bisabolol, free-radical scavengers such as vitamin E and its derivatives, soothing agents such as cornflower water, iris extract, depigmenting agents, biological active agents such as urea, amino acids, vitamins and their derivatives, proteins, salicylic acid and its derivatives, $\alpha$-hydroxy acids, pyrrolidonecarboxylic acid and its salts, and ceramides.

The skilled worker will of course choose any possible complementary compound or compounds, and/or the quantity thereof, so as to not or not substantially alter the advantageous properties of the composition according to the invention as a result of the intended addition.

The composition according to the invention preferably has a skin-respecting pH, generally a pH ranging from 5 to 8 and preferably from 5.5 to 7.5.

The composition according to the invention can be packaged in any kind of package. In particular, the cleansing and/or makeup remover compositions according to the invention may advantageously be packaged in a one-dose (or single-dose) pack, i.e., a pack whose contents can be used completely in the course of a single use. A pack of this kind may in particular be obtained in accordance with the prior art, especially by extrusion blow-molding of a plastic. This technique therefore makes it possible for a container to be blow-molded, filled with the composition and then sealed in a single operation which is both aseptic and continuous.

In a first stage, the polymer, in particular in granule form, can be extruded, which also makes it possible to sterilize it. A two-part molding device may be closed over the extruded polymer in order to form the body of the container. It is then possible to inject, inside the mold, a gas such as sterile filtered air, which will make it possible to "inflate" the container in accordance with the form of the mold. The pack thus obtained can subsequently be filled with the cleansing composition according to the invention, the composition preferably having been sterilized beforehand. When the required volume is filled, the pack can be closed. A technique of this kind is described in particular in the article "Sterility and versatility in cosmetic cream packaging" by D. Wilson, in Cosmetics and Toiletries Manufacture Worldwide, pages 253–256, the disclosure of which is incorporated herein by reference.

Another subject of the invention, therefore, is a composition for cleansing and/or removing makeup from the skin, mucosae, and/or eyes, comprising at least one homogeneous polyholoside, characterized in that the composition is packaged in a single-dose pack.

The invention is illustrated in more detail in the following examples.

EXAMPLES

Example 1

Eye Makeup Remover Lotion

| | |
|---|---|
| chitosan lactate | 0.5 g |
| allantoin | 0.1 g |
| cornflower water | 3 g |
| rosewater | 0.5 g |
| preservative | qs |
| water | qs for 100 g |

This lotion, which contained no surfactant, permitted efficient removal of makeup from the eyes. Moreover, it was particularly suitable for sensitive eyes.

Example 2

Eye Makeup Remover Lotion

| | |
|---|---|
| sodium hyaluronate | 0.05 g |
| allantoin | 0.1 g |
| cornflower water | 3 g |
| rosewater | 0.5 g |
| preservative | qs |
| water | qs for 100 g |

This lotion, which contained no surfactant, permitted efficient removal of makeup and was particularly suitable for sensitive eyes.

Example 3

Biphase Makeup Remover Lotion

| | |
|---|---|
| aqueous phase (55% by weight) | |
| chitosan lactate | 0.5 g |
| copper salt | 0.04 g |
| preservative | qs |
| water | qs for 100 g |
| fatty phase (45% by weight) | |
| vaseline oil | 15 g |
| volatile silicone oil | 55 g |
| 2-ethylhexyl palmitate | 30 g |

A biphase lotion was obtained which permitted simple and effective removal, even of waterproof makeup.

Example 4

Makeup Remover Milk for the Face and Eyes

| | |
|---|---|
| dextran | 0.5 g |
| 2-ethylhexyl palmitate | 25 g |
| glycerol | 3 g |
| carboxyvinyl polymer | 0.5 g |
| NaOH | 0.3 g |
| preservative | qs |
| water | qs for 100 g |

This composition was in the form of a makeup removing milk having good cosmetic properties, and was gentle and comfortable to use.

Example 5

Makeup Remover Milk for the Face and Eyes

| | |
|---|---|
| sodium hyaluronate | 0.05 g |
| 2-ethylhexyl palmitate | 25 g |
| glycerol | 3 g |
| carboxyvinyl polymer | 0.5 g |
| NaOH | 0.3 g |
| preservative | qs |
| water | qs for 100 g |

This composition was in the form of a makeup removing milk having good cosmetic properties, and was gentle and comfortable to use.

Example 6

Face Makeup Remover Gel

| | |
|---|---|
| sodium hyaluronate | 0.05 g |
| glycerol | 3 g |
| Carbomer | 0.8 g |
| karité butter | 1 g |
| alcohol | 5 g |
| preservative | qs |
| water | qs for 100 g |

This composition was in the form of a makeup removing gel having good cosmetic properties.

Example 7

Makeup Remover Cream

| | |
|---|---|
| sodium hyaluronate | 0.01 g |
| 2-ethylhexyl palmitate | 10 g |
| volatile silicone oil | 10 g |
| apricot kernel oil | 7 g |
| stearyl alcohol | 5 g |
| potassium stearate | 0.5 g |
| sorbitan stearate + sucrose cocoate | 4 g |
| xanthan gum | 0.3 g |
| preservative | qs |
| water | qs for 100 g |

This composition was in the form of a makeup removing cream having good cosmetic properties.

Example 8

Eye Makeup Remover Lotion

| | |
|---|---|
| sodium hyaluronate | 0.05 g |
| allantoin | 0.1 g |
| honey | 0.3 g |
| poloxamer 184 | 1 g |
| cornflower water | 3 g |
| rosewater | 0.5 g |
| preservative | qs |
| water | qs for 100 g |

This lotion, which contained a surfactant, permitted effective removal of makeup from the eyes.

Example 9

Comparative

Two aqueous solutions were prepared containing, in one case 0.5% by weight of chitosan lactate, and in the other case 0.05% by weight of sodium hyaluronate.

Test 1: The makeup removal power of these two solutions was compared with that of water and that of a commercial makeup remover.

The makeup removal power was determined with the aid of the so-called robotic makeup remover technique:

The apparatus was composed of a plate and an arm which was fitted with a weight, and subjected the plate to a pressure of 100 g/cm$^2$, one of the ends of which arm was equipped with a swab which slid on the plate.

A fine layer of a black waterproof mascara, sold under the trademark Keracils by Lancôme, was applied to the plate. This plate was dried for 4 hours.

A cotton swab impregnated with 1 ml of the composition to be tested was then passed in one direction over the plate 8 times, the swab being replaced after each pass.

A visual evaluation was made of the quantity of mascara remaining on the plate after the 8 passes. The 8 passes corresponded to ideal makeup removal with a commercial makeup remover used as a reference.

It was observed that the makeup removal power of the two solutions comprising a polyholoside according to the invention was greater than that of water and also superior to that of the commercial makeup remover.

Test 2: These results were confirmed by an in vivo test carried out on 10 human subjects.

The solutions according to the invention were tested in comparison with the commercial makeup remover (control) for a period of at least 3 days.

Three criteria were evaluated: the makeup removal power, the cosmetic characteristics (gentleness, smoothness, etc.) and comfort.

The following results were obtained:
  solution comprising chitosan lactate:
    makeup removal power identical to that of the control
    cosmetic characteristics identical to those of the control
    comfort superior to that of the control
  solution comprising sodium hyaluronate:
    makeup removal power superior to that of the control
    cosmetic characteristics superior to those of the control
    comfort superior to that of the control

We claim:

1. A makeup removing composition for the skin, mucosae or eyes, said composition consisting essentially of at least one homogeneous polyholoside present in an amount effective to remove makeup from the skin, mucosae or eyes, wherein said at least one homogeneous polyholoside is a hyaluronic acid derivative wherein said composition does not comprise a surfactant.

2. A composition according to claim 1, wherein said at least one homogeneous polyholoside is substituted by at least one substituent selected from amino groups and fatty chains.

3. A composition according to claim 2, wherein said fatty chains contain from 8 to 30 carbon atoms.

4. A composition according to claim 1, wherein said at least one homogeneous polyholoside is present in linear or branched form.

5. A composition according to claim 1, wherein said hyaluronic acid derivative is a metal salt.

6. A composition according to claim 5, wherein said hyaluronic acid derivative is sodium hyaluronate.

7. A composition according to claim 1, wherein said at least one homogeneous polyholoside is present in said composition in a quantity ranging from 0.01 to 5% by weight, relative to the total weight of the composition.

8. A composition according to claim 7, wherein said at least one homogeneous polyholoside is present in said composition in a quantity ranging from 0.02 to 1% by weight, relative to the total weight of the composition.

9. A composition according to claim 1, wherein said composition is in the form of an emulsion, an optionally gelled aqueous solution, a lotion, a cream, a milk or a mousse.

10. A composition according to claim 9, wherein said lotion is a biphase lotion.

11. A composition according to claim 10, wherein said composition is packaged in a single-dose pack.

12. A method of preparing a makeup removing composition for the skin, mucosae or eyes, said composition consisting essentially of at least one homogeneous polyholoside, wherein said at least one homogeneous polyholoside is a hyaluronic acid derivative, said method comprising the step of including in said composition said at least one homogeneous polyholoside in an amount effective to remove makeup from the skin, mucosae or eyes.

13. A method according to claim 12, further comprising the step of including in said composition a cosmetically or dermatologically acceptable vehicle.

14. A method according to claim 12, wherein said at least one homogeneous polyholoside is present in an amount effective to cleanse the skin, mucosae, and/or eyes, and/or in an amount effective to remove make-up from the skin, mucosae, and/or eyes.

15. A method according to claim 12, wherein said composition causes little or no irritation or has a gentle feel.

16. A method according to claim 12, wherein said composition is a gelled composition.

17. A method according to claim 12, wherein said at least one homogeneous polyholoside is substituted by at least one substituent selected from amino groups and fatty chains.

18. A method according to claim 17, wherein said fatty chains contain from 8 to 30 carbon atoms.

19. A method according to claim 12, wherein said at least one homogeneous polyholoside is present in linear or branched form.

20. A method according to claim 1, wherein said hyaluronic acid derivative is a metal salt.

21. A method according to claim 20, wherein said hyaluronic acid derivative is sodium hyaluronate.

22. A method according to claim 12, wherein said at least one homogeneous polyholoside is present in the final composition in an amount ranging from 0.01 to 5% by weight, relative to the total weight of the composition.

23. A method according to claim 22, wherein said at least one homogeneous polyholoside is present in the final composition in an amount ranging from 0.02 to 1% by weight, relative to the total weight of the composition.

24. A method according to claim 12, wherein said composition does not comprise a surfactant.

25. A method according to claim 12, wherein said composition is in the form of an emulsion, an optionally gelled aqueous solution, a lotion, a cream, a milk or a mousse.

26. A method according to claim 25, wherein said lotion is a biphase lotion.

27. A method according to claim 12, wherein said composition contains a surfactant in an amount less than an amount effective to remove makeup from the skin, mucosae or eyes.

* * * * *